(12) United States Patent
Von Mandach

(10) Patent No.: US 10,265,142 B2
(45) Date of Patent: Apr. 23, 2019

(54) KIT AND SYSTEM FOR ASSEMBLING AN ORTHODONTIC BRACKET

(71) Applicant: Christoph Von Mandach, Bözberg (CH)

(72) Inventor: Christoph Von Mandach, Bözberg (CH)

( * ) Notice: Subject to any disclaimer, the term of this patent is extended or adjusted under 35 U.S.C. 154(b) by 0 days.

(21) Appl. No.: 15/126,630

(22) PCT Filed: Mar. 12, 2015

(86) PCT No.: PCT/EP2015/055135
§ 371 (c)(1),
(2) Date: Sep. 16, 2016

(87) PCT Pub. No.: WO2015/140026
PCT Pub. Date: Sep. 24, 2015

(65) Prior Publication Data
US 2017/0086948 A1   Mar. 30, 2017

(30) Foreign Application Priority Data

Mar. 18, 2014 (CH) ........................ 0411/14

(51) Int. Cl.
*A61C 7/28* (2006.01)
*A61C 7/08* (2006.01)
(Continued)

(52) U.S. Cl.
CPC ................ *A61C 7/285* (2013.01); *A61C 7/08* (2013.01); *A61C 7/141* (2013.01); *A61C 7/30* (2013.01); *B21D 39/03* (2013.01)

(58) Field of Classification Search
CPC ........... A61C 7/285; A61C 7/08; A61C 7/141; A61C 7/30; B21D 39/03
See application file for complete search history.

(56) References Cited

U.S. PATENT DOCUMENTS 2,257,069 A * 9/1941 Peak ..................... A61C 7/12
433/15
2,665,480 A   1/1954 Johnson
(Continued)

FOREIGN PATENT DOCUMENTS

| CN | 201710487 U | 1/2011 |
| EP | 1 847 232 | 10/2007 |

(Continued)

OTHER PUBLICATIONS

English translation of the International Preliminary Report with Written Opinion for PCT/EP2015/55135 dated Sep. 20, 2016, 9 pages.
(Continued)

*Primary Examiner* — Cris L. Rodriguez
*Assistant Examiner* — Hao D Mai
(74) *Attorney, Agent, or Firm* — Paul D. Bianco; Katharine Davis; Fleit Gibbons Gutman Bongini & Bianco PL

(57) ABSTRACT

A kit for an orthodontic bracket, which includes at least a base plate and a flap that can be pivoted over the base plate, to which a flap directly or indirectly guided wire bow can be fastened. The kit includes a selection of base plates and flaps differing in size and shape. Base plates and flaps are produced from sheet metal by bending and stamping. The two parts can be connected to each other without a shaft by being pivoted in relation to each other.

18 Claims, 10 Drawing Sheets

(51) Int. Cl.
  *A61C 7/14* (2006.01)
  *A61C 7/30* (2006.01)
  *B21D 39/03* (2006.01)

(56) References Cited

U.S. PATENT DOCUMENTS

| | | | | |
|---|---|---|---|---|
| 2,958,945 A * | 11/1960 | Waldman | A61C 7/12 | 433/15 |
| 3,043,006 A * | 7/1962 | Wallshein | A61C 7/30 | 433/11 |
| 3,218,713 A * | 11/1965 | Wallshein | A61C 7/12 | 433/11 |
| 3,414,976 A * | 12/1968 | Steiner | A61C 7/12 | 433/15 |
| 3,464,113 A * | 9/1969 | Silverman | A61C 7/00 | 433/11 |
| 3,477,129 A * | 11/1969 | Rubin | A61C 7/14 | 433/11 |
| 3,543,404 A * | 12/1970 | Rubin | A61C 7/30 | 433/11 |
| 4,023,274 A * | 5/1977 | Wallshein | A61C 7/30 | 433/11 |
| 4,077,126 A * | 3/1978 | Pletcher | A61C 7/285 | 433/10 |
| 4,083,113 A * | 4/1978 | Miller | A61C 7/282 | 433/17 |
| 4,144,642 A * | 3/1979 | Wallshein | A61C 7/30 | 433/11 |
| 4,249,898 A * | 2/1981 | Andrews | A61C 7/12 | 433/21 |
| 4,299,569 A * | 11/1981 | Frantz | A61C 7/141 | 433/8 |
| 4,355,975 A * | 10/1982 | Fujita | A61C 7/143 | 433/11 |
| 4,382,781 A * | 5/1983 | Grossman | A61C 7/30 | 433/17 |
| 4,419,078 A * | 12/1983 | Pletcher | A61C 7/285 | 433/10 |
| 4,487,581 A | 12/1984 | Adler | | |
| 4,498,867 A * | 2/1985 | Kesling | A61C 7/282 | 433/16 |
| 4,523,908 A * | 6/1985 | Drisaldi | A61C 7/146 | 433/3 |
| 4,551,094 A * | 11/1985 | Kesling | A61C 7/30 | 433/17 |
| 4,559,012 A * | 12/1985 | Pletcher | A61C 7/285 | 433/10 |
| 4,712,999 A * | 12/1987 | Rosenberg | A61C 7/285 | 433/11 |
| 4,859,179 A * | 8/1989 | Kesling | A61C 7/30 | 433/16 |
| 5,154,606 A * | 10/1992 | Wildman | A61C 7/12 | 433/8 |
| 5,356,288 A * | 10/1994 | Cohen | A61C 7/14 | 433/10 |
| 5,358,402 A * | 10/1994 | Reed | A61C 7/141 | 433/10 |
| 5,380,196 A * | 1/1995 | Kelly | A61C 7/141 | 433/10 |
| 5,474,444 A * | 12/1995 | Wildman | A61C 7/12 | 433/18 |
| 5,618,176 A * | 4/1997 | Andreiko | A61C 7/28 | 433/10 |
| 6,142,775 A * | 11/2000 | Hansen | A61C 7/12 | 433/14 |
| 8,246,348 B2 * | 8/2012 | Heiser | A61C 7/285 | 433/10 |
| 8,333,586 B2 * | 12/2012 | Kantomaa | A61C 7/143 | 433/10 |
| 2004/0157185 A1 * | 8/2004 | Andreiko | A61C 7/16 | 433/9 |
| 2004/0157186 A1 * | 8/2004 | Abels | A61C 7/285 | 433/10 |
| 2004/0166457 A1 | 8/2004 | Devincenzo | | |
| 2005/0227196 A1 * | 10/2005 | Von Mandach | A61C 7/16 | 433/9 |
| 2005/0255422 A1 | 11/2005 | Cordato | | |
| 2007/0243497 A1 | 10/2007 | Voudouris | | |
| 2009/0081603 A1 | 3/2009 | Forster | | |
| 2010/0000069 A1 * | 1/2010 | Voudouris | A61C 7/28 | 29/460 |
| 2010/0075269 A1 * | 3/2010 | Mutschler | A61C 7/00 | 433/10 |
| 2012/0202163 A1 * | 8/2012 | Vashi | A61C 7/14 | 433/8 |
| 2015/0021210 A1 * | 1/2015 | Kesling | A61C 19/02 | 206/63.5 |

FOREIGN PATENT DOCUMENTS

| | | |
|---|---|---|
| EP | 2039318 A2 | 3/2009 |
| JP | H0312147 A | 1/1991 |
| JP | 2005211313 A | 8/2005 |

OTHER PUBLICATIONS

International Search Report for PCT/EP15/55135 dated May 19, 2015 (with English translation).
Written Opinion for PCT/EP15/55135, dated Sep. 24, 2015.
Search report for Chinese Patent Application 2015800256059 (related to U.S. Appl. No. 15/126,630) dated Aug. 20, 2018.
European Search Report dated Jun. 4, 2018 for European Application No. 18166561.3-1126.

\* cited by examiner

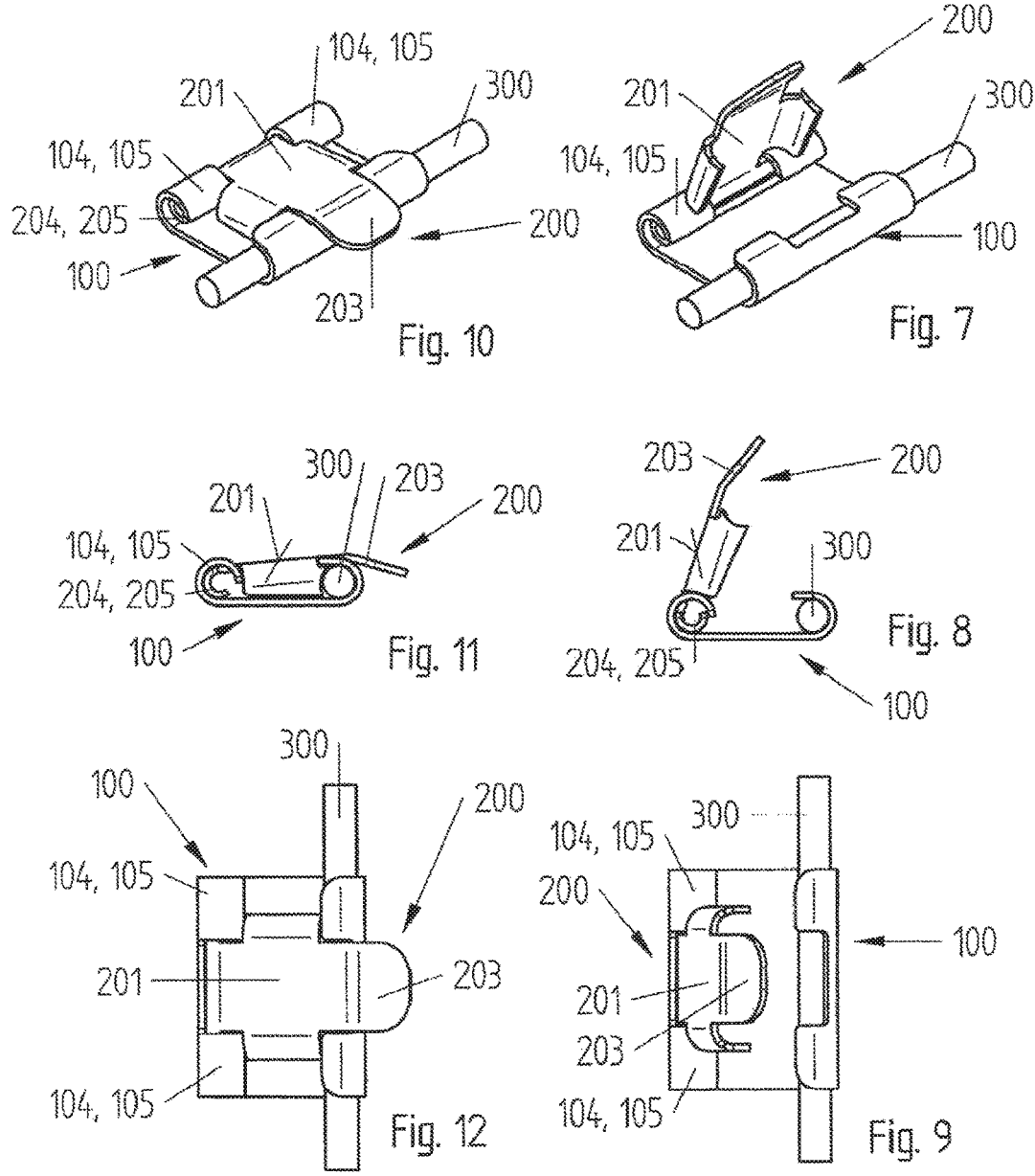

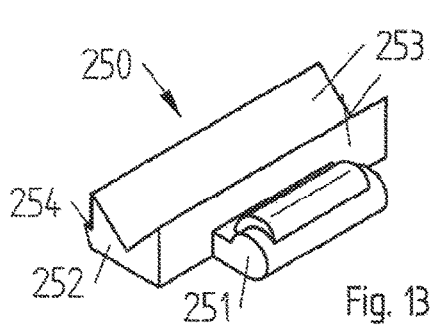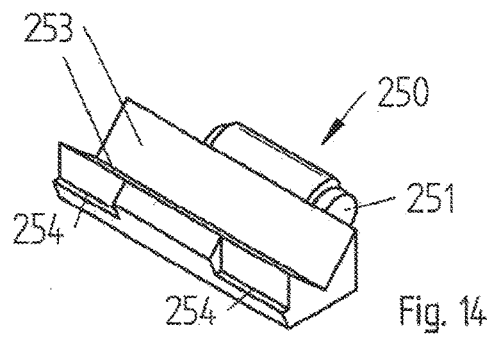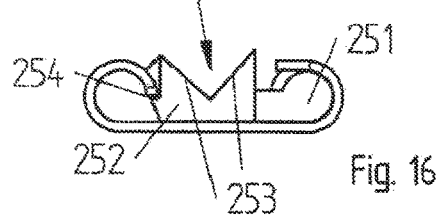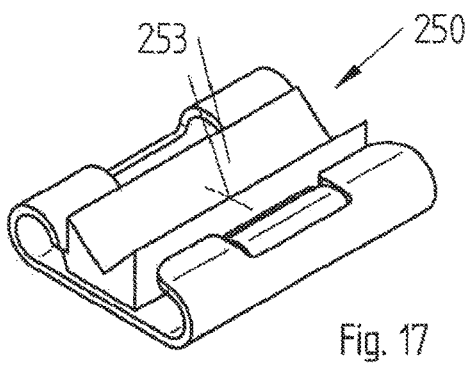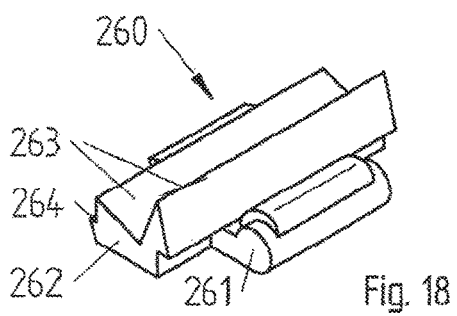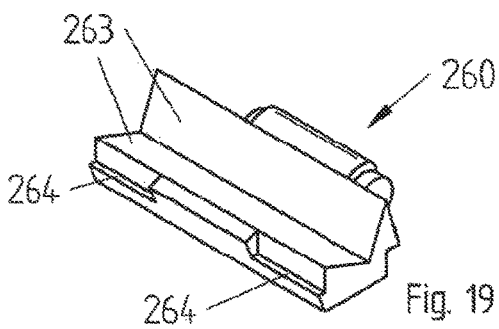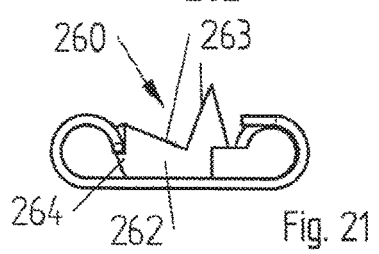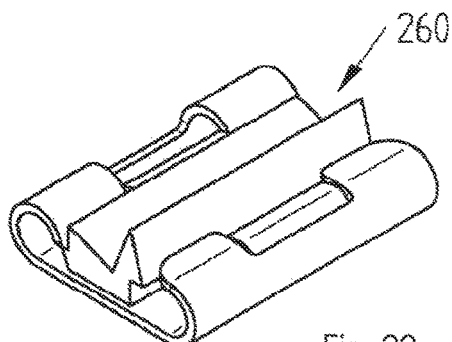

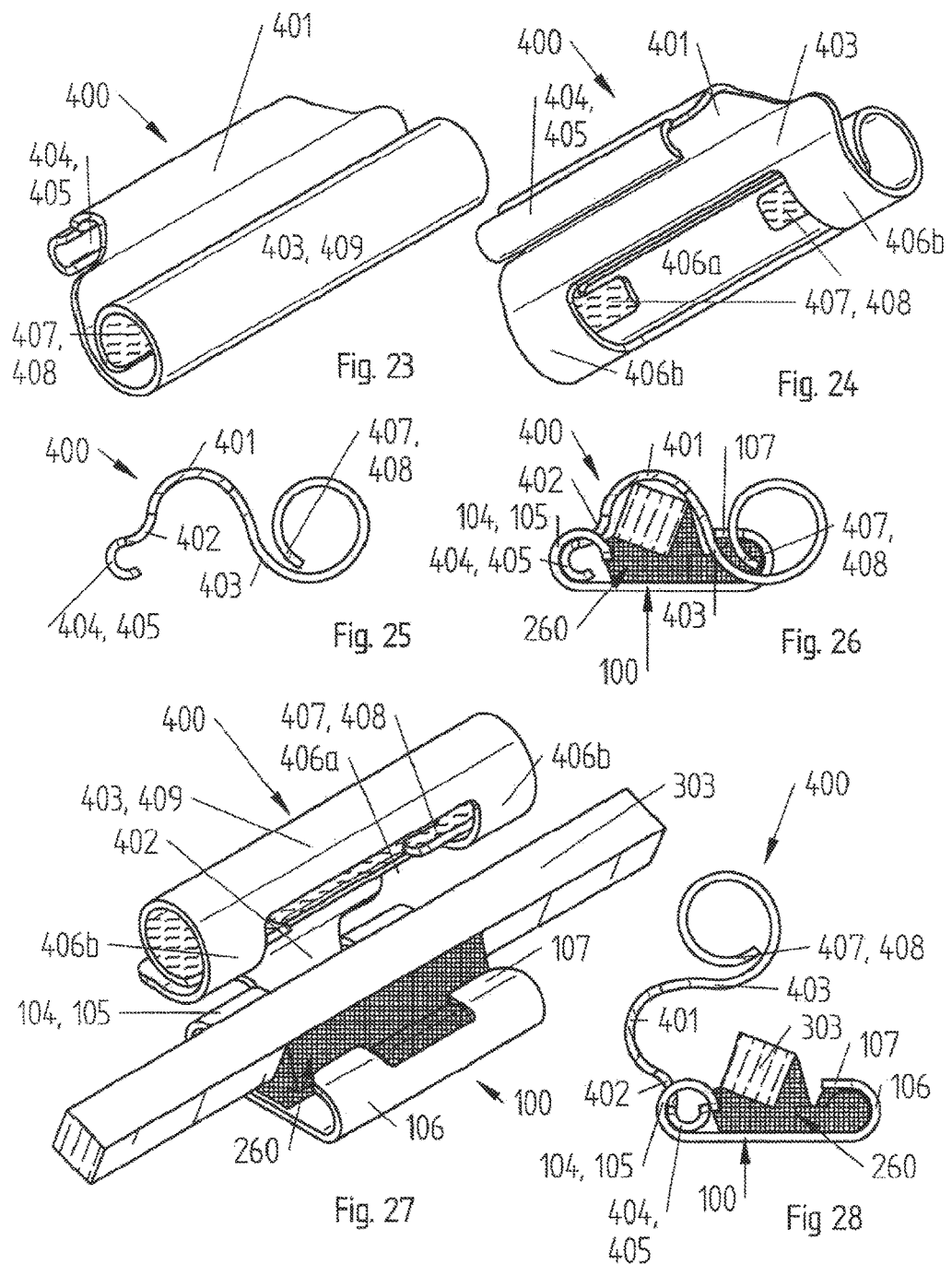

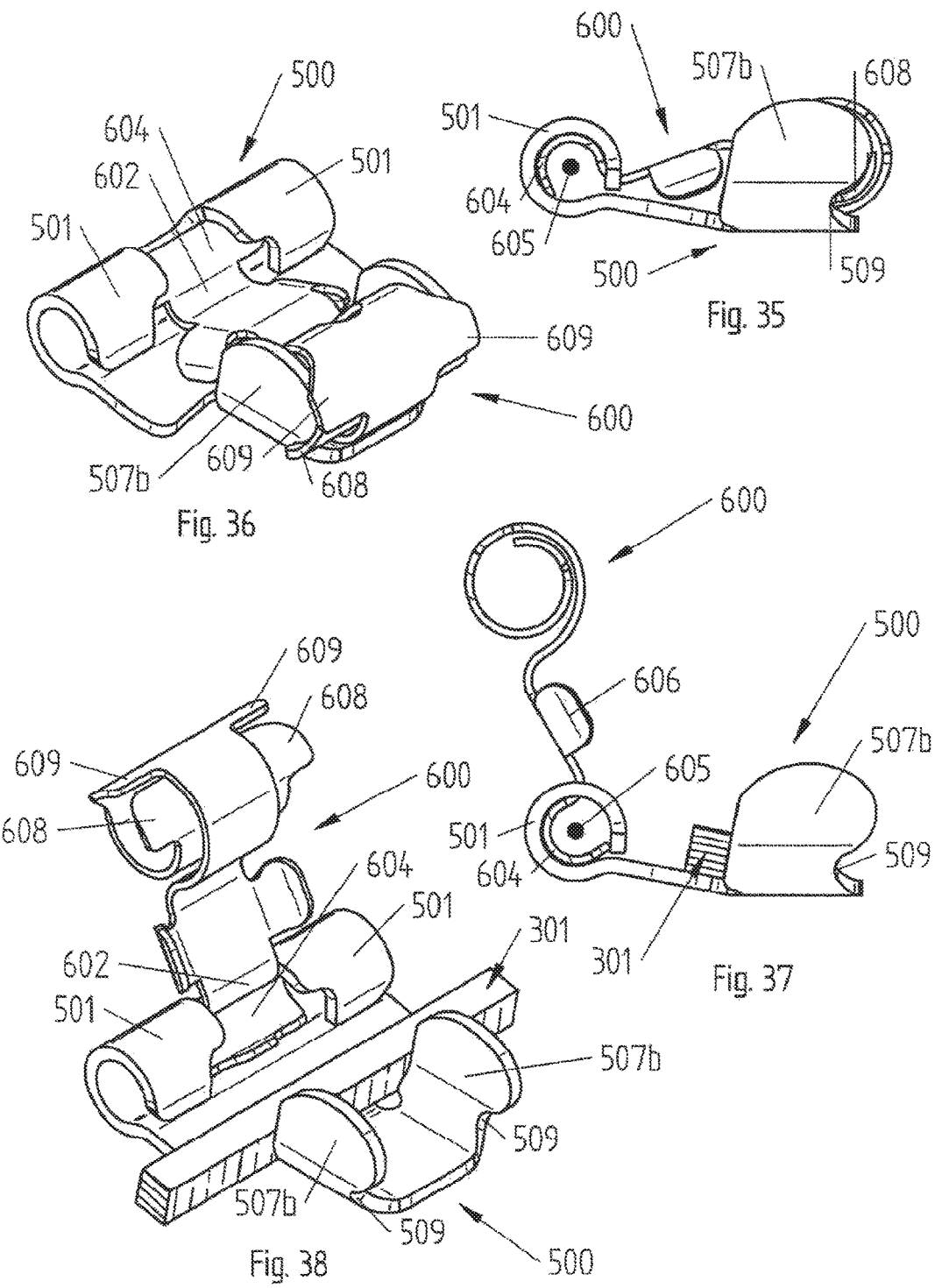

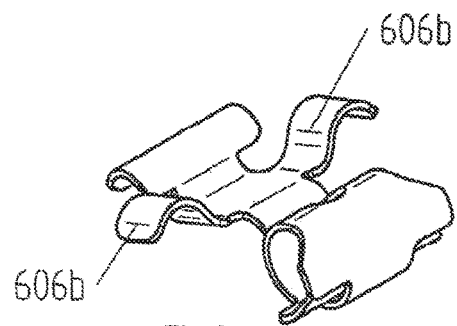
Fig 39
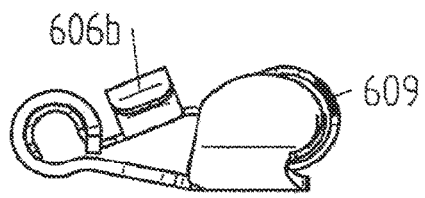
Fig. 40
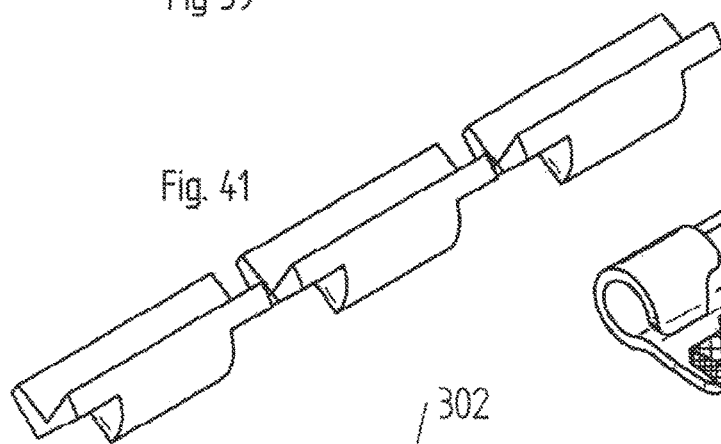
Fig. 41
Fig. 43
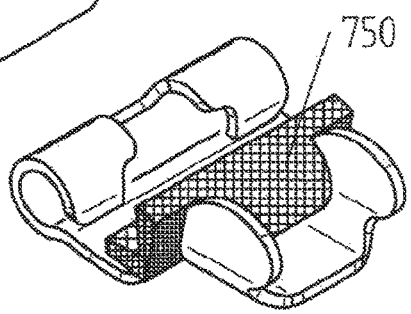
Fog 42
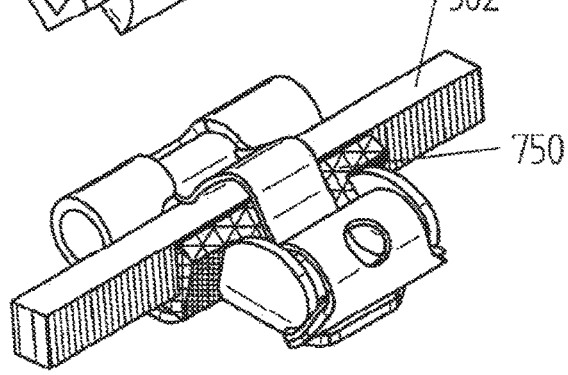
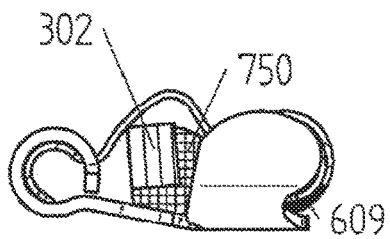
Fig. 44
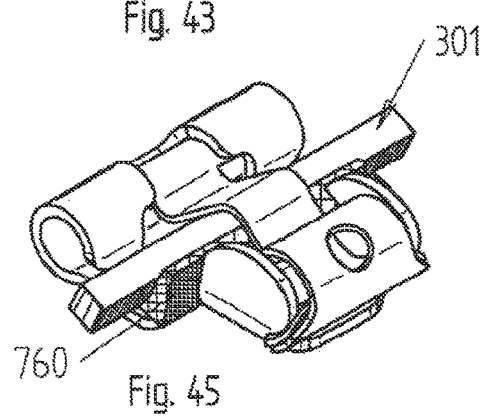
Fig. 45
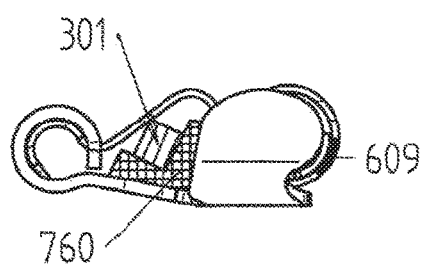
Fig 46

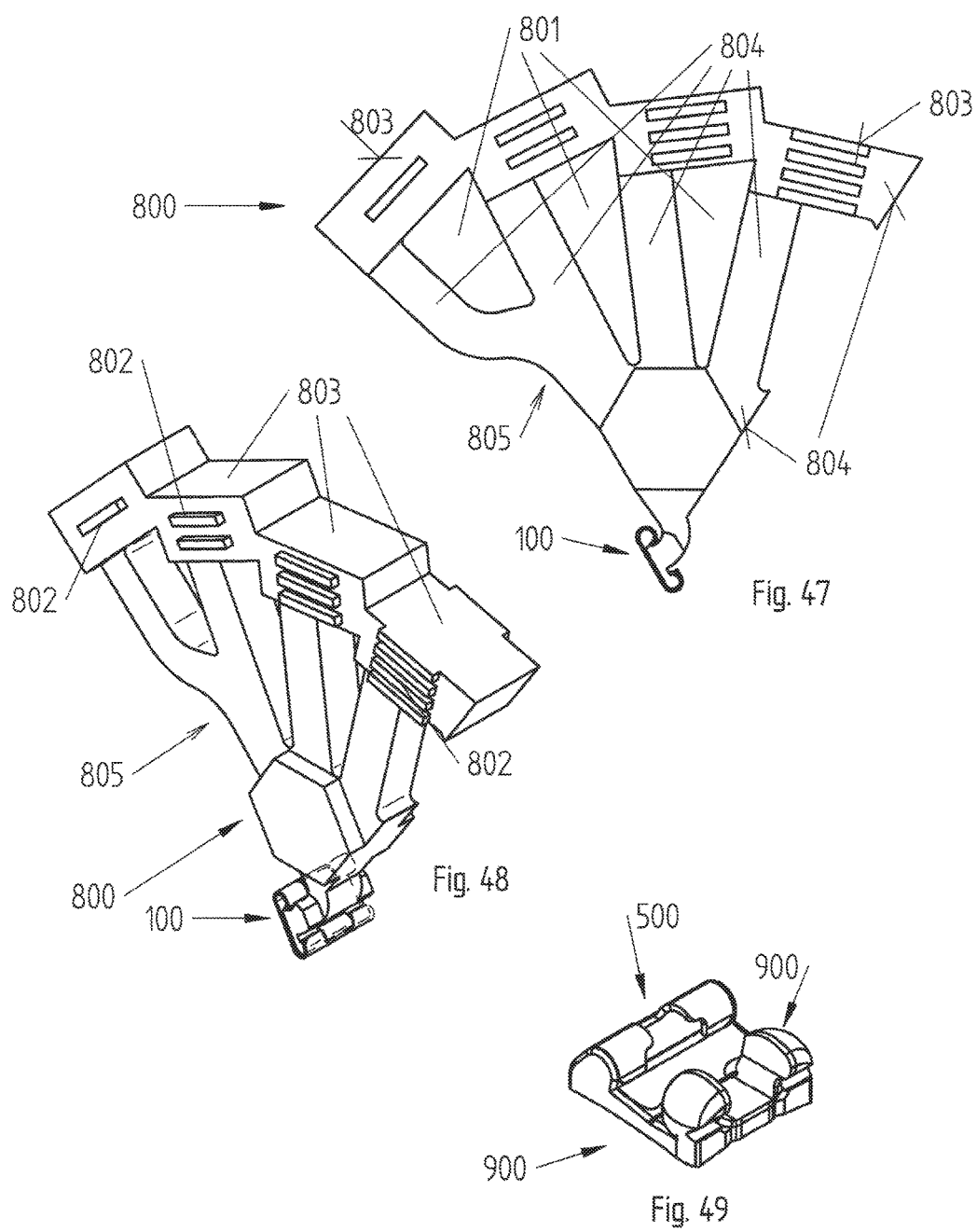

KIT AND SYSTEM FOR ASSEMBLING AN ORTHODONTIC BRACKET

FIELD OF THE INVENTION

The present invention relates to a kit for an orthodontic bracket, said kit comprising at least one base plate and a flap which is pivotable over the base plate and with which a wire arch which is led in the bracket in a direct or indirect manner can be fixed.

BACKGROUND

Orthodontic brackets are obtainable on the market in a very large variety. Today, brackets are manufactured from metal, ceramic and plastic. All these materials require a relatively thick base plate, on which the wire arch lies and which comprises lateral walls forming the so-called slot. With the exception of plastic, these materials have certain a brittleness, and too thin a base plate would significantly affect the strength of the bracket. With the manufacture from plastic, it is not so much the brittleness of the material which is a problem, but rather its elasticity. This elasticity very quickly leads to deformations of the bracket, and this leads to an imprecise guidance of the wire arch in the slot or practically completely blocks the movement of this wire arch in the slot.

These problems have led to orthodontic brackets even today having a relative large construction height, specifically a height of at least 1.5 mm.

It would also be desirable to design the surfaced extension of the bracket or the length of the guidance of the wire as small as possible. It is particularly in the frontal, lower region that the size of the teeth is very small, depending on set of teeth. Most brackets which are available on the market have a slot, whose length is approx. 3 mm. Here too, a reduction of the size is practically impossible with regard to the design of the bracket. This however leads to the space between two adjacent brackets being small. However, in the case that this distance is too small, then only a low deformation possibility of the wire arch exists in practise, in order to be able to carry out the suitable corrective movements.

A further problem with the orthodontic brackets which have been known until now, irrespective of the material selection, lies in the fact that the flaps which secure the wire arch must be realised via a hinge with a corresponding hinge pivot. This cannot be realised with a single, simple manufacturing procedure, but requires a corresponding assembly demanding much effort due to the small size of the brackets. The person carrying out the treatment moreover can only exchange the flaps in the case of few brackets.

The smaller the orthodontic brackets and the more complex the self-ligating mechanics, the greater is the danger of excess cement (adhesive) rendering them functionally unusable. Although smaller brackets are more advantageous with regard to the positioning, since problem zones of a tooth can be better utilised and the bracket therefore also be optimally placed thanks to the small size, this however is at the cost of the exact alignment becoming more demanding, errors becoming more frequent and with these, the fine adjustment requiring significantly more effort at the end of the treatment.

The inventor has already disclosed suitable means which simplify the application of adhesive onto the bracket and the positioning of the bracket on the tooth, in EP 1 482 857. For this, a protector has already been suggested there, and this protector has an equal and opposite hollow shape, in which the bracket to be placed and to be provided with adhesive can be inserted, as well as an applicator which non-positively and possibly holds itself in the bracket and can be removed again after the alignment on the tooth and the hardening/curing of the adhesive or cement. The particularly flat brackets according to the invention can also be simply handled with these aids which are known per se.

SUMMARY OF THE INVENTION

It is now the object of the present invention, to realise a kit for orthodontic brackets, comprising a base plate with a flap which can be pivoted over the base plate and in which a wire arch led directly or indirectly in the bracket can be fixed, in a particularly small manner and especially with an extremely small construction height, said kit permitting many adaptations for force transmission onto the tooth and being able to be applied with different wire arches.

This object is achieved by a kit with a self-ligating bracket, as described herein. Hereby sheet metals of cobalt-chromium alloys are particularly considered.

The new solution is explained as being a kit consisting of a base plate which is to be bonded onto the tooth and in which a hinge bearing is shaped out to the side directed towards the occlusion, into which hinge bearing a flap as an exchangeable spring is pivoted, forming a hinge, said flap on closure pressing a wire arch in the embodiment of an insert part into two surfaces running perpendicularly to one another. The earlier edgewise slot is now reduced to two perpendicular planes by way of this exchangeable insert part, and the usual brackets with different slot dimensions are replaced by a freely selectable flap which presses the wire arch onto the perpendicular planes of the insert part. The system first and foremost is based on the force which originates from the flap, and not on the positive fitting of the wire arch in the slot. The essential element for control of the force is the flap, which is preferably designed as a scroll spring.

The search for the smallest and, at the same time, most stable components as bracket bases and bracket flaps, according to the invention leads to combined stamping and bending technology. The solution which has been found brings the orthodontic wire arch to the surface of the tooth to approx. 0.35 mm, and with a miniature embodiment even to 0.15 mm. The wire arch therefore respectively lies 0.25 mm and 0.45 mm closer to the tooth than with the previously smallest bracket. The profile at the height of the wire and at the chewing side of this, further measures 1.3 mm at the most, and with the miniature embodiment as a whole only 0.65 mm. The previously smallest bracket demanded rubber O-rings and in comparison measured at least 1.7 mm.

Phynox®, a cobalt-chromium-nickel alloy which is not only suitable for dental application, but is also approved for long-term implantation due to its excellent characteristics and properties, contributes to the optimisation of the inventive bracket of the kit. In particular, this alloy has the property of being extremely processing/machining friendly as a rolled sheet, by way of this being easy to cut, stamp and deform, and at 530° Celsius and 3 hours of heat treatment, without deforming, being able to be converted into a material which with regard to strength and spring stiffness beats the hardest of steels. The function of the kit according to the invention and with a bracket and an insert part is explained as follows: two planes which are perpendicular to one another and onto which a spring designed as a flap presses the orthodontic wire arch, serve instead of a groove or a slot as is the case with the edgewise or tip-edge bracket. The greater the force, the greater is also the torque transmission transversely to the course of the wire arch. However, a torque is also transmitted along the course of the wire arch, and one with respect to the rotation position of the tooth. The torque along the wire arch course, with regard to orthodontics is called alignment or angulation, in contrast to the inclination which concerns the torque and the plane perpendicular to the course of the wire arch.

The kit according to the invention and with exchangeable insert parts avoids the common effect of the jamming of a wire arch in the slot. This is due to the fact that the rigid slot is formed by only two contact surfaces which run perpendicularly to one another, and this is now replaced by a selectable, suitable flap in the form of an elastic spring. The promotion of the movement of a tooth as perpendicularly as possible to the wire arch entails large forces, and these result in corresponding dimensions of the wire arch. The congruence between the wire arch and the slot increases with size, and as a result a clamping or jamming effect tends to set in. This is particularly due to the fact that square wire arches are prone to small damage and shape changes, which they undergo as a result of the act of chewing and the application duration. Concluding, it can therefore be said that the flap with the previous brackets has served predominantly for securing the position of the wire arch in the slot, but has only been of a minor significance concerning the exertion of force upon the tooth to be moved, whereas the solution according to the invention gives the wire arch new freedom of movement, prevents a clamping or jamming and the flap executes a force-regulating effect.

It is particularly advantageous if a first edge of the base plane forms a region which is rolled in by more than 180° and less than 360°, into a hinge bearing, wherein a rolled-in edge of the flap which acts as a bearing pivot can be introduced in this region and can be assembled into a hinge by way of a relative pivoting of both parts to one another. A separate pivot can be avoided by way of this.

A further preferred embodiment envisages the second edge lying opposite the first edge being rolled in by 180° and directly or indirectly serving the guidance of the wire arch. If the wire arch has a round shape in cross section, then this can be directly inserted into this edge rolled in by 180°. If the flap is now pivoted into the closed condition, then the flap arrests (locks) the wire arch. For this, the flap as well as the second edge of the base plate preferably comprises positive-fit means, which come into engagement with one another on closure of the flap. The kit according to the invention envisages an insert part serving the mounting and guiding of a wire arch with a rectangular cross section being positively and non-positively held in the second edge.

BRIEF DESCRIPTION OF THE DRAWINGS

Further advantageous embodiments are to be deduced from the claims, and their significance and manner of acting are explained in the subsequent description with reference to the accompanying drawings.

There are shown in:

FIGS. 7-12 show the base plate according to FIGS. 1-3 and the flap according to FIGS. 4-6 assembled into a complete bracket.

FIGS. 13-15 show different views of a first insert part.

FIGS. 16-17 show the insert part of FIGS. 13-15 inserted into a bracket.

FIGS. 18-20 show a second insert part.

FIGS. 21-22 show the insert part of FIGS. 18-20 inserted into a bracket.

FIGS. 23-25 show a second embodiment of a flap for engagement with the base plate according to FIGS. 1-3.

FIGS. 26-28 show the flap of FIGS. 23-25 assembled with the base plate and engaged with an insert part, in a closed position (FIG. 26) and an open position (FIG. 28).

FIGS. 35-38 show the base plate according to FIGS. 29-31, engaged with the flap of FIGS. 32-34, in an open position (FIGS. 37-38) and in a closed position (FIGS. 35-36), without (FIGS. 35-36) and with (FIGS. 37-38) an inserted wire arch.

FIG. 39 shows a perspective view of a further variant of a flap.

FIG. 40 shows the flap of FIG. 39 engaged with a base plate according to FIGS. 29-31.

FIG. 41 shows several insert parts which are connected via predetermined breaking locations, for engaging with a base plate according to FIGS. 29-31.

FIGS. 42-46 show the insert parts of FIG. 41 engaged with a base plate according to FIGS. 29-31, wherein the insert parts of the FIGS. 42-44 vary in inclination angle of the contact surfaces for a wire arch, depending on the desired torque angle.

FIGS. 47-48 show two views of a torque-determining element, inserted in a base plate.

FIG. 49 shows a base plate with a protector.

DETAILED DESCRIPTION OF THE INVENTION

The concept of the present invention and which is in accordance with the invention lies very generally in forming or shaping self-ligating brackets from sheet metal. Hereby, one particularly uses non-rusting spring steel alloys or cobalt-chromium-nickel alloys, which in particular contain chromium, cobalt, nickel, molybdenum or vanadium. Non-corroding, acid-resistant, sheet metals are particularly suitable. One would preferably apply sheet metals with a thickness between 0.1 and 0.4 mm, in particular between 0.2 and 0.3 mm.

The two bracket parts, specifically the base plate 100 and the flap 200 can be manufactured at high cycle speeds by way of stamping and bending tools. The finished shaped parts are advantageously deburred or the corners rounded, with the barrel finishing method. A cold-rolled, soft cobalt-chromium sheet metal which can be very well machined and subsequently tempered to a very high hardness is used, in order to achieve a sufficient strength with the sheet metals applied here, despite their thinness. Such sheet metals of cobalt-chromium-nickel alloys are known on the market under the trademark Pynox® e.g. from the company Mat-they SA.

The use of sheet metal on manufacture of brackets leads to a large number of different embodiment possibilities, which until now were neither known nor could they be achieved. Various embodiment examples are represented in detail in the present application, and are described in detail hereinafter.

Figure 1:
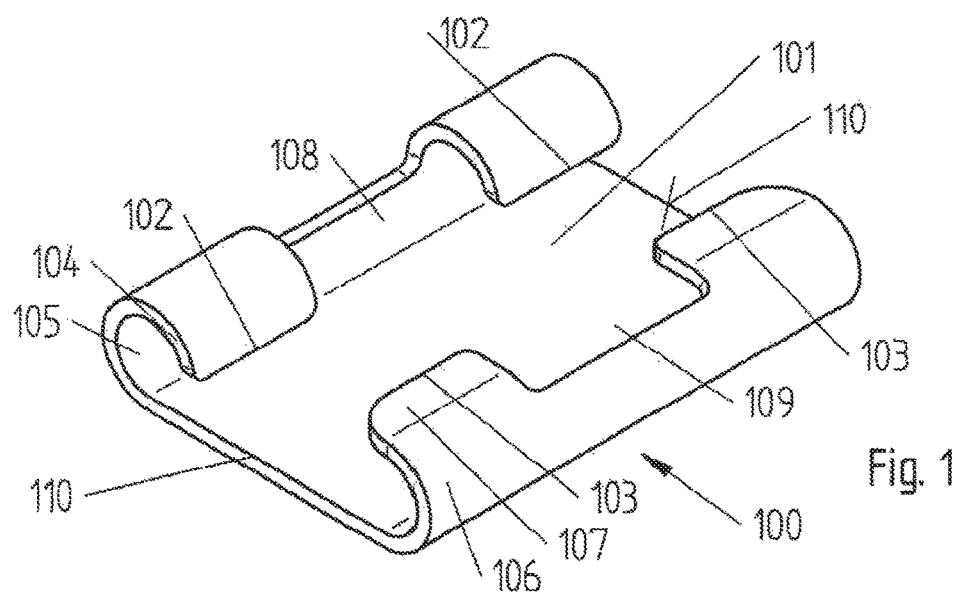
FIG. 1 shows a perspective view of a base plate of the self-ligating bracket according to the invention.
Figure 2:
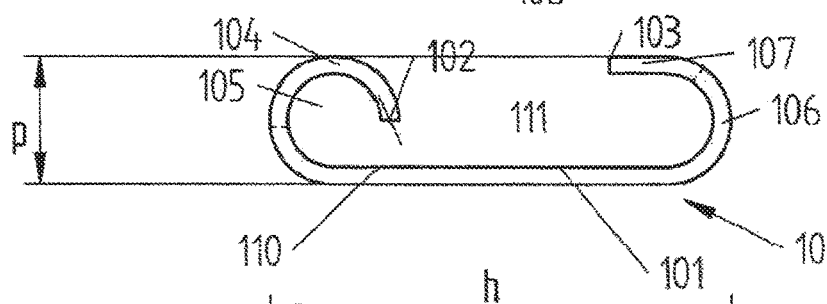
FIG. 2 shows a lateral view of the base plate of FIG. 1.
Figure 3:
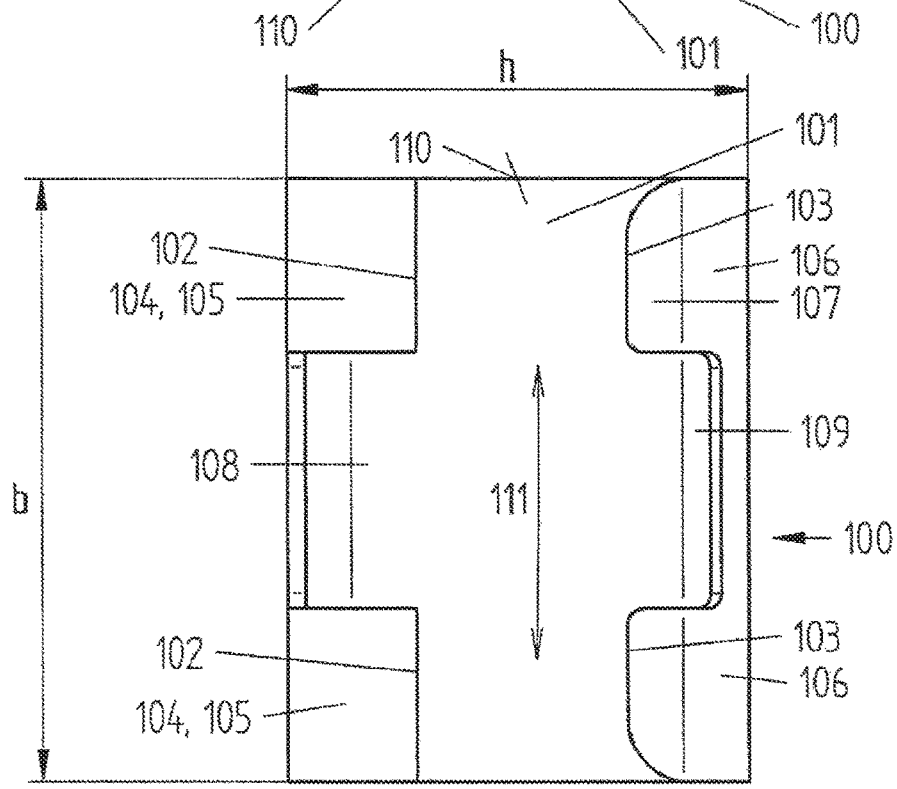
FIG. 3 shows a view from above of the base plate of FIG. 1.

FIGS. 1-3 show a base plate 100 in a first embodiment. This base plate as already specified consists of a corrosion-resistant sheet metal, in particular of a sheet metal of a cobalt-chromium-nickel alloy. The base plate has a base surface 101. This base surface is laterally delimited by two edges 110 which run perpendicularly to the occlusion plane. These edges here are called occlusion edges. A first edge perpendicular to the occlusal edges 110 is indicated at 102 and a second edge at 103. These two edges are rolled in after the stamping. This can be recognised most clearly in the lateral view in FIG. 2. The rolled-in region of the first edge 102 is indicated at 104, whereas the rolled-in region of the second edge 103 is indicated at 106. The first rolled-in region 104 is rolled in by more than 180° and less than 360°. More preferably, as is represented here, the roll-in angle is between 240° and 300°. In particular, this roll-in angle is 270°, as is represented in the figure. This rolled-in region 104 of the first edge forms a hinge bearing 105 for a flap 200 which is not represented here.

The rolled-in region 106 of the second edge 103 lies directly opposite the first rolled-in region 104 of the first edge 102. Here, the roll-in angle is at least approximately 180°. The rolling-in does not begin directly at the second edge 103, but offset slightly inwards, so that a horizontal end-region 107 arises. This quasi horizontal end-region 107 runs roughly parallel to the base surface 101. It can be advantageous to design this so-called horizontal end-region 107 inclined towards the base surface 101 by a few degrees, for example 1° and 5°. The reason for this is due to the fact that this second rolled-in region 106 serves for guiding a wire arch 300 which is not yet represented here and is round in cross section, or for holding an insert part. If this quasi horizontal end-region 107 has a slight inclination to the base surface 101, then a wire arch which is round in cross section can be pressed in, amid slight elastic deformation of the rolled-in region 102, wherein the wire arch obtains sufficiency guidance, without this falling out before the wire arch is secured in its position by the flap 200 which is not yet described.

The rolled-in region 104 of the first edge moreover comprises a centrally stamped out pivot recess 108. The rolled-in region 106 of the second edge 103 comprises a likewise central, less deep recess which is indicated as a locking recess 109. The significance of the two recesses is explained later in more detail in the context of the assembled bracket.

Figure 4:
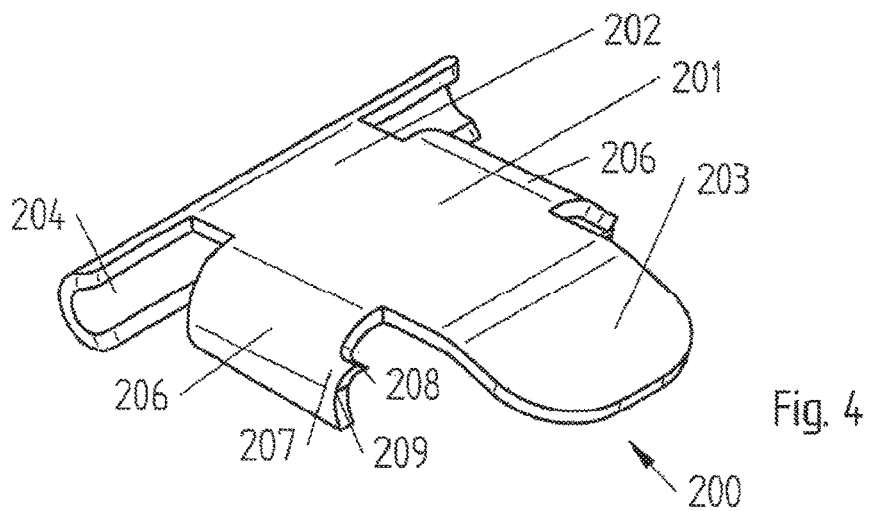
FIG. 4 shows a perspective view of a flap configured to engage the base plate according to FIGS. 1-3.
Figure 5:
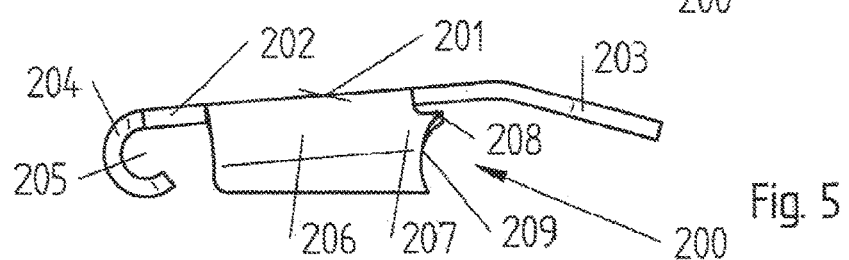
FIG. 5 shows the flap of FIG. 4 in a lateral view.
Figure 6:
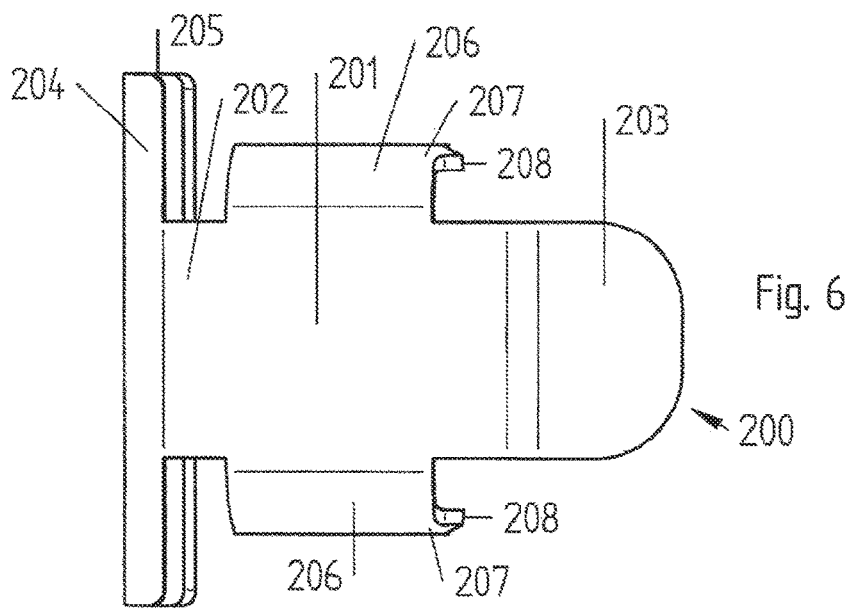
FIG. 6 shows a view from above of the flap of FIG. 4.

The flap 200 is represented in each case on its own in the various views in FIGS. 4-6. FIG. 4 shows the flap 200 in a perspective view. The flap has a flat roof region 201 which is connected to a rolled-in region 204 via a neck 202. This rolled-in region 204 forms a hinge pivot 205. The flat roof region 201 at the region opposite to the hinge pivot 205 is angled slightly downwards and forms a pressing tab 203. This pressing tab 203 here is designed in a semi-round manner at the end. A lateral wing 206 is integrally formed in each case at both sides, laterally on the flat roof region 201. The two wings 206 at the side edges which are directed in the direction of the pressing tab comprise positive-fit means 207. These positive-fit means 207 here are designed in the form of arresting lugs 208. A rounded edge region 209 runs from the tip of the arresting lugs 208 to the lower end of the respective wing 206. This rounded edge region 209 has a radius which at least approximately corresponds to the radius of a wire arch 300 to be inserted. This will be dealt with once again later.

The complete bracket, consisting of a base plate 100 and flap 200 is represented in the assembled, open condition in FIGS. 7-9. A wire arch section is represented in a purely symbolic manner for explanation, since the complete wire arch is of course very much longer. The wire arch 300 itself is not part of the bracket, but a suitable product available on the market can be used for this. These wire arches with regard to their dimensions is specified in inches. These wire arches or these arches either consist of steel or nickel titanium with a so-called memory effect. These wire arches with a round cross section are not commonly used, although being obtainable on the market. For this reason, insert or inlay parts are applied for wire arches with a rectangular cross section, as is yet to be described.

The flap, pivoted by more than 90° is led to the base plate 100 such that the neck 202 of the flap 200 comes to lie in the pivot recess 108 of the rolled-in region 104 of the first edge 102, for the assembly of the bracket consisting of the base plate 100 and the flap 200. The rolled-in region 204 of the flap 200 now rolls into the rolled-in region 104 of the first edge 102, by way of a pivot movement of the flap 200 in the closure direction. The radius of the rolled-in region 104 of the first edge 102 with respect to its inner diameter is preferably designed slightly smaller than the outer diameter of the rolled-in region 204 of the flap 200. The rolled-in region 104 of the first edge 102 from now is spread slightly and the rolled-in region 204 of the flap 200 is slightly pressed together, on joining together. This leads to the flap remaining in each opened intermediate position, and the treating orthodontic physician having free access, in order to insert the wire arch 300 into the rolled-in region 106 of the base plate 100 or into an insert part. It is particularly from the lateral view according to FIG. 7 that one can now recognise how the rolled-in region 104 of the first edge becomes a hinge bearing 105, and the rolled-in region 204 of the flap 200 now acts as a hinge pivot 205.

The bracket is now described as is shown in the FIGS. 7-9, in the closed condition, in the two FIGS. 10-12. FIG. 10 thereby shows a perspective view, FIG. 11 a lateral view and FIG. 12 a plan view, onto the bracket. In the closed condition, the pressing tab 203 engages over the rolled-in region 106 of the second edge 103. Hereby, the pressing tab 203 comes to lie in the region of the locking recess 109. The complete bracket remains extremely flat on account of this, and a torque on the flap 200 is accommodated in the arresting recess 109. This is yet further encouraged by the lateral wings 206. The arresting lug 208 thereby engages below the free end of the second rolled-in region 106 of the second edge, which is to say the horizontal end-region 107. The flap 200 is locked or arrested in its position relative to the base plate 100 with this. The positive-fit means 207 thus forms a positive fit with the second edge 103 of the base plate 100. In the closed condition of the bracket, the rounded edge 109, subsequent to the locking lug 208 to the bottom, now bears on the wire arch 300. The wire arch 300 is now likewise fixed in its desired position.

A first embodiment example of an insert part 250 which serves for mounting and guiding a wire arch with a rectangular or square cross section, is represented on its own in different views, in the FIGS. 13-15. This first embodiment of the insert part is indicated in its entirety at 250. It moreover comprises a continuation 251 which with regard to shape is designed such that the continuation 251 positively and/or non-positively fits into the bent-over region of the second edge 103 of the bracket base plate 100. This embodiment of the bracket base plate corresponds to the miniature embodiment which has a particularly low height of the base plate. The continuation 251 is integrally formed on a centre section 252 as one piece. Two guide surfaces 253 are formed in this centre section, at an angle of 90° to one another. This prismatic guidance is designed such that the guide surfaces 253 in the installed condition in the bracket base plate enclose an angle of 45° to the base surface 101 of this bracket base plate. A retention continuation 254 which serves for receiving the first edge 102 of the base plate 100 is integrally formed opposite to the continuation 251. As is evident, the continuation 251 comprises a centric bead which thickens the continuation and which in the installed condition of the insert part 250 in the base plate 100 engages into the arresting recess 109 of the bent-over region 106 of the second edge 103. The insert part is secured against lateral displacement by way of this. The insert part is likewise held perpendicularly with respect to the lateral displacement, on the one hand by way of the continuation 251 positively lying in the bend-over 104 of the first edge and on the other hand the second edge 103 pressing upon the retention continuation. The insert part 250 is held in the base plate 101 in a manner secured in all directions by way of this.

This situation is clearly evident from the FIGS. 16 and 17.

A second embodiment of the insert part is now represented in FIGS. 18-20. This second embodiment is indicated at 260. This embodiment also has a continuation 261 which positively and/or non-positively fits into the bent-over region of the second edge 103 and on the opposite side of a centre section 262 again comprises a retention continuation 264 which interacts with the first edge 102 in the installed condition. Here too, again two guide surfaces 263 are present at an angle of 90° to one another. However, one guide surface hereby has an inclination of about 20° to the base surface 101 of the base plate 100 in the installed condition, whereas the other guide surface 263 therefore as an inclination of 70° to the base surface 101. The retention of the insert part 260 in the base plate 100 is thus maintained in the same manner. This is evident from the FIGS. 21 and 22.

FIGS. 23-25 show an alternative form of a flap, which here is indicated at 400. Whereas the first embodiment of the flap 200 is relatively rigid, this flap in contrast is designed as a spring. This flap 400 also has a first rolled-in region 404 with a small radius, serving as a hinge pivot 405, and an arched roof region 401 which here however is designed in a waved manner. A region 403, which is rolled in a roughly snail-like (spiral-like) manner and which is indicated as a scroll spring, serves as a pressing or holding tab. The scroll spring 403 likewise comprises a positive-fit means which serves for engaging over a correspondingly adapted base plate in the rolled-in region 106, and with its arched roof region 401 serves for pressing a wire arch 303 with a rectangular cross section into the desired position.

FIGS. 26-28 show the application of the base plate 100 with an insert part 250 for the guidance of a wire arch 303 with a rectangular cross section. The scroll spring 403 engages over this insert part 250, as is represented in the FIGS. 13-22. Hereby, a recess 406a in the scroll spring permits an encompassing of the bent-over region 106 of the second edge 103 of the base plate 100, by way of the lateral guide regions 406b. Positive-fit recesses 407 in the scroll spring 403 permit the positive engagement of the end-piece 107 into the scroll spring 403. Hereby, the edge of the positive-fit recess 407 acts as an arresting lug 408.

With this embodiment of the flap as a scroll spring, a neck 402 is also present between the roof region 401 and the bending 404 serving as a hinge pivot 405. The scroll spring here moreover comprises at least one bead as a transverse strut 409, which runs parallel to the hinge pivot 405 and is integrally formed into the scroll spring.

Figure 29:
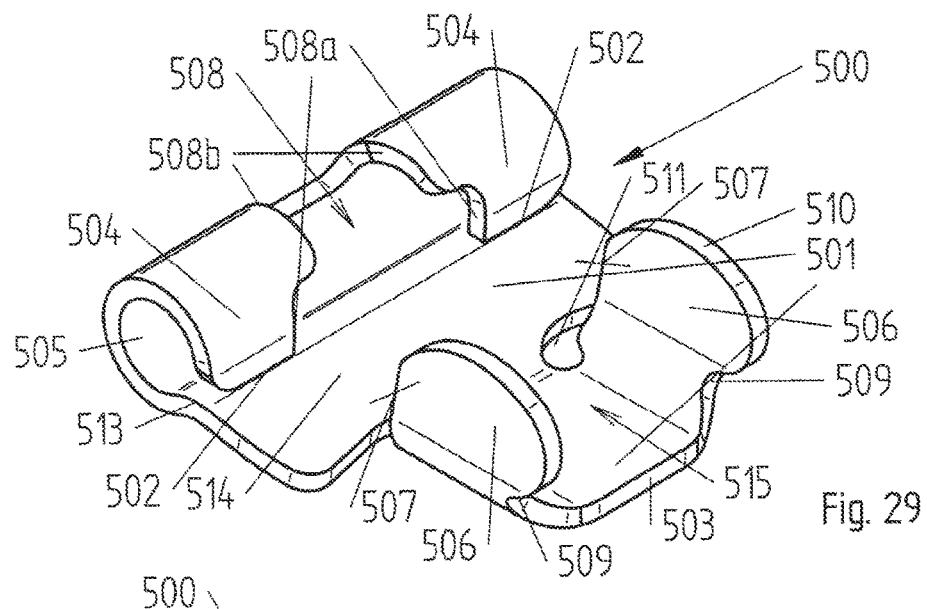
FIGS. 29-31 show a second embodiment of a base plate.
Figure 30:
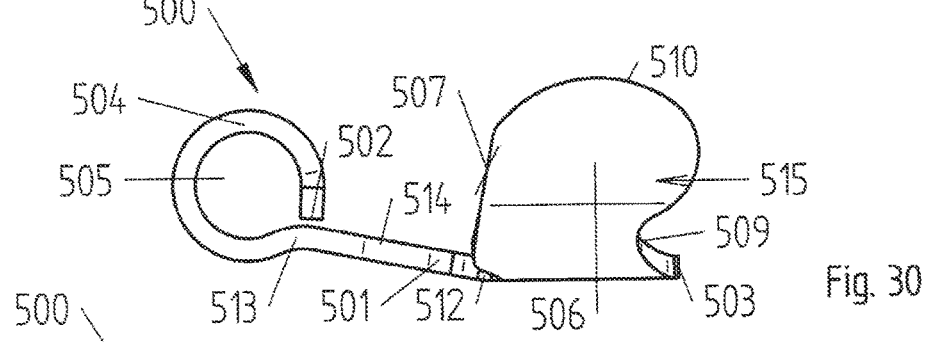
Figure 31:
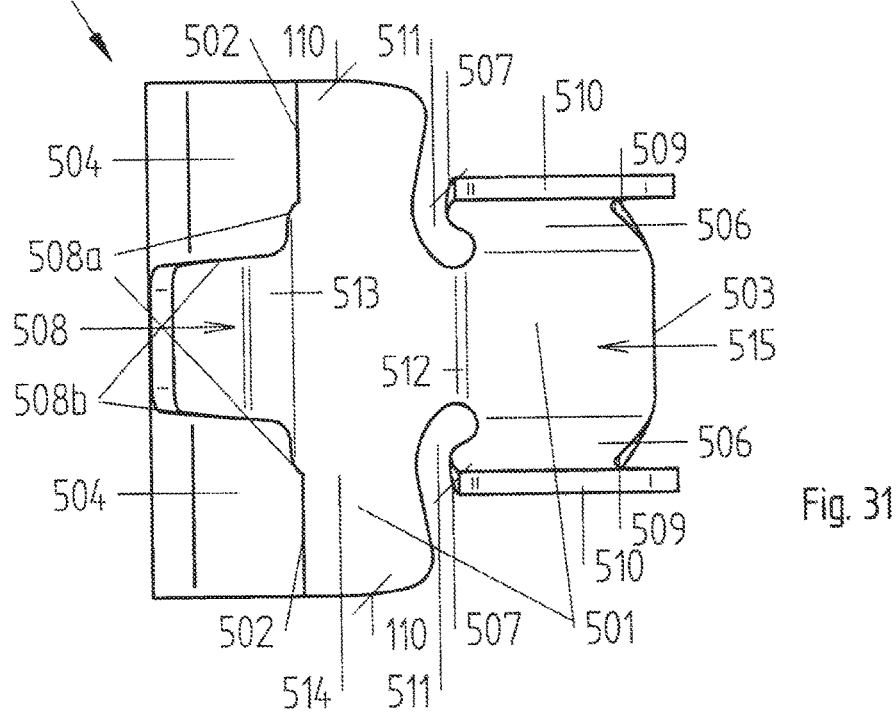

A second embodiment of a base plate for forming an orthodontic bracket is now represented in FIGS. 29-31. This second embodiment of the base plate is indicated at 500. This base plate 500 also has a base surface 501. Its first edge 502 has a bent-over region 504. This bent-over region 504 forms a hinge bearing 505. A second edge 503 is present opposite the first edge 502. The base surface 501 of the base plate 500 is delimited by two indentations 511 which lie opposite one another and these form the limitation of two side edge sections 506 which lie opposite one another, and are bent up in a parallel manner, perpendicularly to the base surface 501 of the base plate. The base surface 501 runs further between these two bent-over side edge sections 506, up to the second edge 503. The bent-over side edge sections 506 have edges 507 which are aligned to the occlusion plane.

The bent-over region 504 of the first edge 502 again has a pivot recess 508. This pivot recess 508 has a widening 508a for introducing the flap. The pivot recess 508a then tapers into a narrowing 508b which serves for securing the flap and the fixation of this in the opened position.

Arresting recesses 509 are recessed on the bent-over side edge sections 506, opposite the edges 507 aligned to the occlusion plane. These arresting recesses serve for the fixation of the flap 500 in the closed condition. The side edge sections 506 have a rounded upper edge 510 which serves for the wearing comfort. The shape of the indentations 511 in the side edges serving for delimiting to the side edge sections bent over to the top can be seen most clearly in FIG. 31. As is known, the tooth surfaces are not plane and accordingly the base surface of the base plate 501 has a first bending 512 and a second bending 513 which both serve for the adaptation to the anatomy of the tooth. This however is not absolutely necessary, since the unevenesses of the tooth can be compensated by the cement 900 due to the small size of the base plate 500. The region 515 in the condition assembled on the tooth runs vertically which is to say perpendicularly to the edges 507. A protective guide channel for the flap, as is yet to be described by way of FIGS. 35-38, runs between the two bent-over side edge sections 506.

Figure 32:
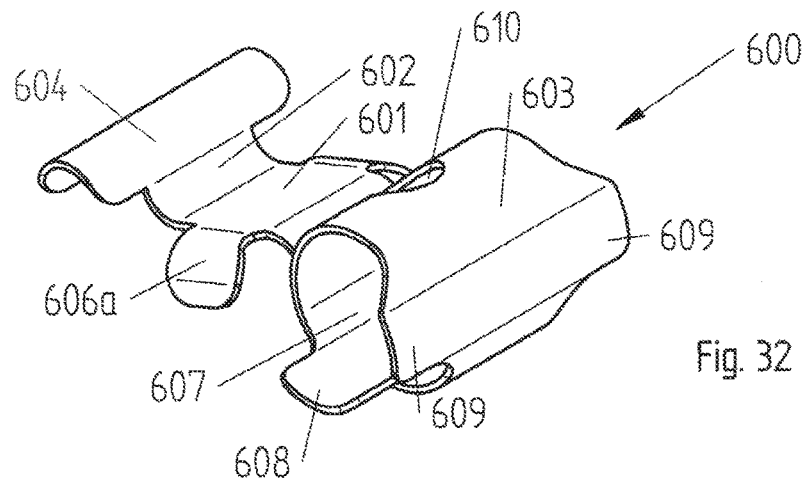
FIGS. 32-34 show a flap which engages the base plate of FIGS. 29-31.
Figure 33:
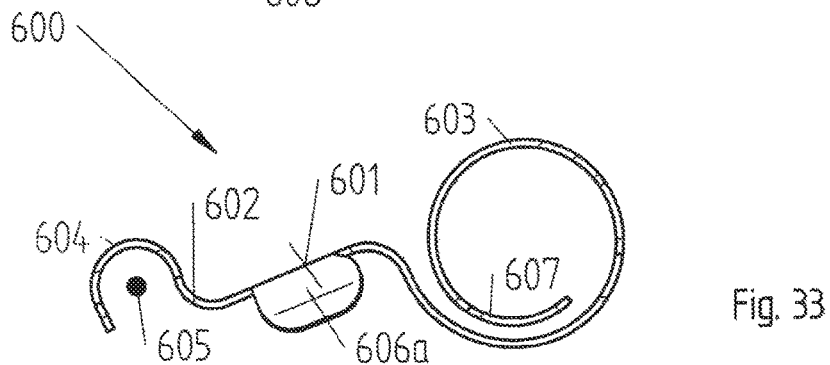
Figure 34:
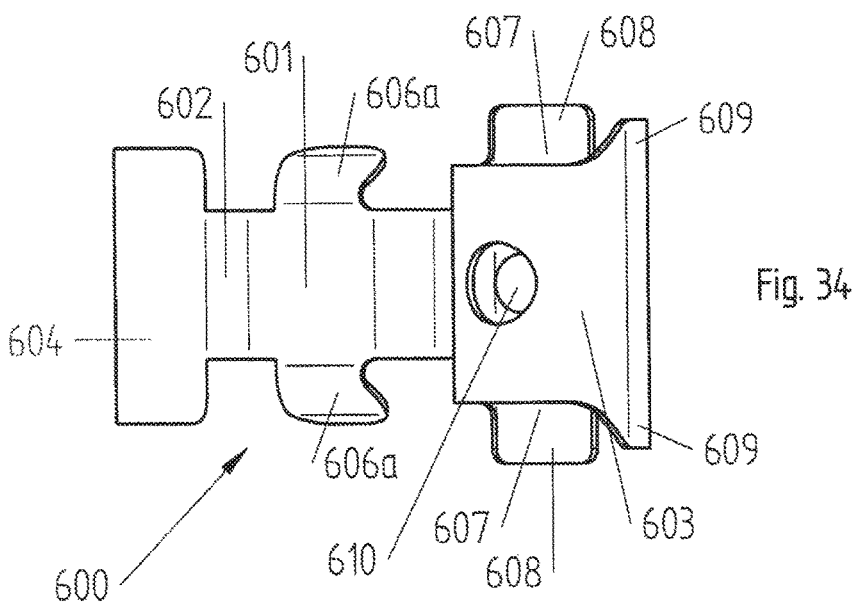

A second embodiment of a flap is represented in the FIGS. 32-34. This flap is indicated in its entirety at 600. It again has a flat roof region 601, to which a neck 602 connects, subsequent to which neck a bent-over part 604 with a small bending radius again follows. The centre of this bending 604 forms the hinge pivot 605 which is not present on the body. Two lateral wings 606 are integrally formed on the roof region 601. In the embodiment according to FIGS. 32-34, these lateral wings 606 are bent over from the flat roof region 601 in the direction of the base plate 500. With one variant, as is shown in FIGS. 39 and 440, these lateral wings are bent more to the top and thus in particular serve for the attachment of ligatures or for rubber chains or elastics, if this should be necessary. These specially shaped lateral wings are indicated at 606b.

A pressing tab as part of a scroll spring 603 is formed and shaped connecting to the flat roof region 601, at the side which lies opposite the neck 602. This scroll spring has laterally projecting arresting lugs 608 as positive-fit means 607. These arresting lugs 608 in the closed condition of the flap 600 engage into side edge sections 506 of the base plate 500. A bead for securing against overload can be additionally provided. This bead is indicted at 609. A bore 610 as an aid for opening the flap 600 is recessed in the pressing tab 603 designed as a scroll spring.

The flap 600 according to the FIGS. 32-34 is now represented in Figures FIGS. 36-38 assembled with the base plate 500 according to the FIGS. 29-31, in the closed condition whilst omitting the wire arch. A square arch 31 is now applied in the FIGS. 37 and 38, whereas the flap 605 is still shown in the opened condition. Here, the wire arch 301 with the correct cross section is used without the aid of an insert part. Thereby, the one edge of the wire arch lies directly on the base surface 501, whereas the other side edge of the wire arch comes to bear on the edges 507. With this embodiment of the bracket too, the base plate is mostly applied in combination with different shapes of insert parts which are indicated here at 750. FIG. 41 shows how several such insert parts can be manufactured shaped into a rod and are separably connected to one another via predetermined breakage locations. The insert parts 750 in turn comprise a continuation, which here comes to lie between the two bent-over side edge sections. They however also yet bear on the edges 507 of these bent-over side edge sections 506. Thereby, one would design the continuation such that this is positively and non-positively held between the two parallel side edge sections. Again, these insert parts can have different inclinations of the guide surfaces relative to the base surface and accordingly one insert part is indicated at 750 whereas a second one with a different inclination to the base surface is indicated at 760, as is to be seen in FIGS. 45 and 46. The lateral wings 606 have been completely omitted with the embodiments according to the FIGS. 43-46, since these are not absolutely necessary.

The two FIGS. 47 and 48 finally show a gauge for estimating the torque. In combination with this, the insert parts 250, 260, 750 are graded such that they each differ by an angle of 6.6°. As with lingual 2D bracket systems which are common today, the base plates according to the invention and with the reference numeral 100 are not directed to the inclination, but only to the height with respect to the occlusion plane, the angulation and the rotation. First and foremost, one wishes to achieve a minimal construction profile with this. The bracket according to the invention moreover is to additionally permit the precise adjustment of the individual teeth with square wires. The minimal construction height, on account of the use of the rolled-in region of the second edge 106 serves for the maximum comfort of the patient during the usually common levelling phase which also always begins with round wires. The need and wishes of the patient are also often filled already with the levelling in many cases. However, if a more extensive adjustment of the individual teeth is necessary, and square wires are required, then the gauge serves for estimating the torque, in order to determine the alignment of the base plate according to the invention, with respect to the occlusion plane. The gauge can be clamped into the base plate, by which means the relation to the occlusion pane can be unhurriedly estimated via the direction indicator, on the patient. If for example it is precisely perpendicular to the marking 3, then the respective insert element is to be selected. If it tends to lie perpendicularly to the marking 2 or 4, then depending on the extent, that one which matches more to 3 or indeed more to 2 or 4 is to be selected. Recesses 801 improve the visibility. Indictors 803 are present and these are provided with the characterisations 802 and each characterise different alignments with respect to the occlusion planes, with a difference of 20° in each case. The indicators 803 are integrally formed on arms 804 running perpendicularly to the occlusion plane. Finally, a recess 805 for the incisal ridge is present. Finally, FIG. 49 shows a base plate 100, which here is held on a tooth which is not represented, by way of cement 900. A protector 900 is attached, in order to ensure that the cement does not get into the region of the rolled-in regions or onto the upper side of the base plate. The protector 900 thus positively receives the base plate whilst leaving the bonding surface free. An applicator can then be put over the protector after the attachment, and this simplifies the positioning on the tooth.

The two main constituents of the kit, specifically the base plate and the flap are manufactured of a sheet metal of cobalt-chromium nickel alloy, as already mentioned.

The insert part, apart from the mounting of the wire arches can also serve for the improved retention of aligners. The wire arch as well as the aligner are indicated as orthodontic aids. An insert part can utilise the guide surfaces 253 or can be formed into these retention edges which are positively connectable onto the aligners with equal and opposite shapings, depending of the design of the aligner, for an improved holding of the aligner.

The kit according to the invention, which consists of only three parts, specifically of the base plate and the flap and the insert part, now replaces a huge number of the most different of orthodontic brackets. Despite the fact that two variants of base plates and four variants of flaps, as well as two embodiments of insert parts have been suggested here, these permit a sufficient variety of combination, in order to cover practically all common demands for orthodontic practise, without having to maintain a huge stock of expensive brackets, since here the bracket can be composed by the operator from few parts, and specific to the case in hand.

LIST OF REFERENCE NUMERALS 100 base plate of the bracket
  b=width of the base plate
  h=height of the base plate
  p=profile of the base plate
200 flap
250 insert part
260 insert part
300 wire arch (round)
301 wire arch (rectangular) 0.45 mm×0.55 mm
302 wire arch (rectangular) 0.55×0.70 mm
303 wire arch (square) 0.40×0.40 mm
400 flap as scroll spring
500 base plate, alternative shape
600 flap
750 insert part
760 insert part
800 gauge matching the base plate, for estimating the torque
900 protector
101 base surface of the base plate
102 first edge
103 second edge
104 bent-over region of the first edge
105 hinge bearing
106 bent-over region of the second edge
107 straight, parallel end-piece of the bent-over region 106
108 pivot recess in 104
109 arresting recess in 106
110 side edges
111 protective guide channel for flap 1a
201 flat roof region
202 neck 203 pressing tab
204 bending with a small radius
205 hinge axis
206 lateral wings
207 positive fit means
208 arresting lug
209 rounded edges
250 insert part for guidance
251 continuation engaging into the bent-over region of the second edge
252 centre section
253 guide surfaces at an angle of 90°
254 retention continuation to the first edge
260 insert part, variant
261 continuation into the bent-over region of the second edge
262 centre section
263 guide surfaces at an angle of 90°
264 retention continuation to the first edge
401 arched roof region
402 neck
403 pressing tab as part of the flap 400 which is designed as a scroll spring
404 bending with a small radius
405 hinge pivot
406a recess
406b lateral guide region
407 positive-fit recesses
408 arresting lug
409 transverse strut
501 base surface of the base plate
502 first edge
503 second edge
504 bent-over region of the first edge
505 hinge bearing
506 bent-over side edge section
507 edges directed to the occlusion plane
508 pivot recess
508a widening for introducing the flaps 2a, 2b
508b narrowing for securing the flaps and fixation of the flaps in the opened position
509 arresting recesses
510 rounded upper end of the side edge section
511 indentation of the side edges
512 first bending for adaptation of the bracket base to the anatomy of the tooth
513 second bending for adaptation of the bracket base to the anatomy of the tooth
514 vertical region, or the region aligned perpendicular to the edges 507
515 protective guide channel for the flap 2a and 2b
601 flat roof region
602 neck
603 pressing tab as a scroll spring
604 bending with small radius
605 hinge axis
606 lateral wings, in particular for fine wires
606b lateral wings for rubber chains or elastics
607 positive fit means
608 arresting lug
609 bead for securing against overload
610 bore(s) as aids for opening
700 flap for elastics
750 series of identical torque elements
801 recesses for an improved visibility
802 inscription
803 display of the occlusion plane at an angle of 20° in each case
804 arms for the display of the perpendicular with respect to the occlusion plane
805 recess for the incisal ridges

The invention claimed is:

1. A kit including elements for assembling an orthodontic bracket, the elements of the kit comprising:
   a plurality of base plates for bonding to teeth having different shapes and sizes, each base plate of the plurality of base plates having a first edge rolled inwardly toward a surface of the base plate forming a first recess and a second edge rolled inwardly toward the surface of the base plate forming a second recess directly opposite the first recess so that the first and second recesses face each other to form a slot;
   a plurality of flaps for fixing an orthodontic aid having different shapes and sizes, each flap of the plurality of flaps insertable into the slot by pivotally connecting a first end of said each flap to the first recess of the base plate and by engaging a second end of said each flap to the second recess of the base plate so that each flap of the plurality of flaps is exchangeably connectable to each base plate of the plurality of base plates when assembling the orthodontic bracket; and
   at least one insert part for holding and guiding the orthodontic aid, the at least one insert part insertable into the slot by engaging surfaces with the first and second recesses of the base plate so that the at least one insert part is exchangeably insertable into each base plate of the plurality of base plates when assembling the orthodontic bracket.

2. The kit according to claim 1, wherein the orthodontic aid is an arch wire or an aligner.

3. The kit according to claim 1, wherein the second edge of each base plate of the plurality of base plates is configured for guiding the orthodontic aid and for engaging surfaces of the at least one insert part.

4. The kit according to claim 3, wherein each flap of the plurality of flaps is configured for engagement with the second edge of each base plate of the plurality of base plates.

5. The kit according to claim 3, wherein the orthodontic aid is an arch wire having a round cross section.

6. The kit according to claim 5, wherein the arch wire is configured to be held by the second edge of each base plate of the plurality of base plates.

7. The kit according to claim 1, wherein the first recess of each base plate of the plurality of base plates has a central portion.

8. The kit according to claim 7, wherein each flap of the plurality of flaps has a narrow portion configured for engaging the central portion of the first recess of each base plate of the plurality of base plates.

9. The kit according to claim 1, wherein each flap of the plurality of flaps has a flat surface including wing portions, the wing portions extending laterally from and formed integrally with the flat surface of each flap of the plurality of flaps.

10. The kit according to claim 9, wherein one end of the flat surface of each flap of the plurality of flaps is formed as a pressing tab, the pressing tab extending to a position above the second edge of each base plate of the plurality of base plates and from the position above extending downwardly in a curve toward a plane in which the surface of each base plate of the plurality of base plates lies.

11. The kit according to claim 1, wherein the at least one insert part includes two guide surfaces for the orthodontic aid, the two guide surfaces formed at an angle of 90° to one another.

12. The kit according to claim 1, wherein the at least one insert part is formed from plastic and includes at least one retention continuation configured to engage the first edge of each base plate of the plurality of base plates.

13. The kit according to claim 1, wherein each flap of the plurality of flaps is a spring or a scroll spring, the spring or scroll spring configured for engaging with the first edge of each base plate of the plurality of base plates above the at least one insert part during assembly of the orthodontic bracket.

14. The kit according to claim 13, wherein the spring or scroll spring is configured for pressing the orthodontic aid into position.

15. The kit according to claim 1, wherein each base plate of the plurality of base plates has a length below 2.5 mm, a width below 2.5 mm, and a height below 1 mm.

16. The kit according to claim 1, wherein the plurality of base plates and the plurality of flaps are formed from sheet metal containing a cobalt-chromium-nickel alloy.

17. The kit according to claim 1, wherein the kit further comprises a protector element configured for sealing off an upper side of each base plate of the plurality of base plates and an inside surface of the second edge of each base plate of the plurality of base plates from cement during application of an assembled orthodontic bracket to a tooth.

18. The kit according to claim 17, wherein the kit further comprises at least one applicator element configured for placing over the protector element, for holding a base plate bonded to the tooth, and for enabling desired positioning of the assembled orthodontic bracket to the tooth.

* * * * *